United States Patent [19]

Gitlitz et al.

[11] 4,212,810
[45] Jul. 15, 1980

[54] NOVEL TRIMETHYLTETRAORGANOTIN COMPOUNDS

[75] Inventors: Melvin H. Gitlitz, Edison; John E. Engelhart, Westfield; David A. Russo, Edison, all of N.J.

[73] Assignee: M&T Chemicals Inc., Woodbridge, N.J.

[21] Appl. No.: 971,940

[22] Filed: Dec. 21, 1978

Related U.S. Application Data

[62] Division of Ser. No. 845,354, Oct. 25, 1977, abandoned.

[51] Int. Cl.$^2$ .................. A01N 9/28; C07D 317/50
[52] U.S. Cl. .................. 260/340.5 R; 424/288; 424/245; 260/340.3; 260/429.7; 546/4; 544/225; 549/3
[58] Field of Search .............. 260/340.5 R, 340.3

[56] References Cited

U.S. PATENT DOCUMENTS

| | | | |
|---|---|---|---|
| 3,705,943 | 12/1972 | Kaufman et al. | 424/245 |
| 3,897,553 | 7/1975 | Peterson et al. | 424/245 |
| 3,988,449 | 10/1976 | Buchel et al. | 424/245 |

FOREIGN PATENT DOCUMENTS 3821394 10/1963 Japan .................. 544/225

OTHER PUBLICATIONS

Zasosov, et al, "Chemical Abstracts," vol. 49 (1955), col. 912h–913d.
Chatt, et al. "Chemical Abstracts," vol. 49 (1955), col. 5081f.
Grosjean, et al. "Chemical Abstracts," vol. 58 (1963), col. 6850g.
Pourcel, et al., "Chemical Abstracts," vol. 78, 1973, col. 25965s.

*Primary Examiner*—Donald G. Daus
*Assistant Examiner*—James H. Turnipseed
*Attorney, Agent, or Firm*—Kenneth G. Wheeless; Robert Spector

[57] ABSTRACT

Many varieties of harmful insects which attack useful plant crops can be controlled by treating the plants with compositions containing certain novel tetraorganotin compounds wherein three of the four hydrocarbon groups bonded to the tin atom are methyl and the remaining group is phenyl containing specified substituents or heterocyclic and is either bonded directly to the tin atom or separated from the tin atom by one methylene group. The present compounds exhibit unexpectedly superior insecticidal activity relative to prior art organotin compounds containing three methyl groups and a phenyl or an alkyl- substituted phenyl group bonded to the tin atom.

2 Claims, No Drawings

NOVEL TRIMETHYLTETRAORGANOTIN COMPOUNDS

This is a divisional of application Ser. No. 845,354, filed Oct. 25, 1977, and now abandoned.

BACKGROUND OF THE INVENTION

This invention relates to novel tetraorganotin compounds that effectively control many varieties of insects which are harmful to agricultural and ornamental crops.

The biological activity of compounds containing 3 hydrocarbon radicals bonded to a tin atom is well known. U.S. Pat. No. 3,264,177 discloses that tricyclohexyltin compounds effectively control arachnids, particularly spider mites, however these compounds are generally ineffective as insecticides. The use of certain trialkyltin compounds, including bis(trimethyltin)oxide and trimethyltin chloride as insecticides is disclosed in U.S. Pat. No. 3,702,360. While these trialkyltin compounds effectively control insects, their high phytotoxicity makes them impractical for commercial use.

Compounds containing 4 hydrocarbon groups bonded to a tin atom have for a long period of time been considered to possess, at best, only slight biological activity. In a text entitled "Chemistry of Organotin Compounds" R. C. Poller states that insecticidal activity is largely confined to compounds with three Sn—C bonds. He further states that variations in the nature of the fourth group attached to tin do not produce any striking effects. Despite this general statement a number of organotin compounds wherein the tin atom is bonded to three non-substituted hydrocarbon groups and a fourth hydrocarbon group containing a functional group, which often contains sulfur, have been disclosed as being effective insecticides. Patents claiming this type of organotin compound are discussed in detail in a subsequent portion of this specification.

It is an objective of this invention to provide novel organotin compounds exhibiting useful levels of insecticidal activity.

SUMMARY OF THE INVENTION

This invention provides novel insecticidal tetraorganotin compounds exhibiting a formula selected from the group consisting of

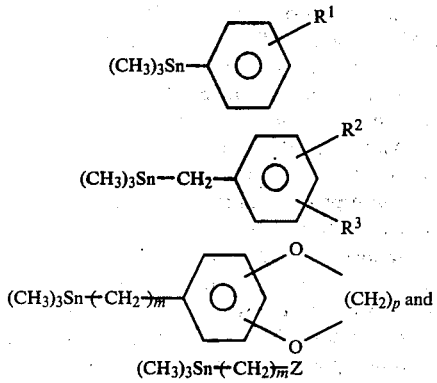

wherein said —O—$(CH_2)_p$—O— group is bonded to adjacent carbon atoms of the phenyl ring, m is 0 or 1, p is 1 or 2, $R^1$ is selected from the group consisting of —$CO_2^\ominus Y^\oplus$, —$CO_2R^4$, —$SO_2OR^5$, —$SO_2R^5$, —$SO_3^\ominus Y^\oplus$, —$PO(OR^5)OR^6$ and —$PO(R^5)R^6$; $R^2$ and $R^3$ are individually selected from the group consisting of hydrogen, fluorine, chlorine, bromine, iodine, aryl, —$OR^4$, —$SR^5$, —$NR^6R^7$, —$N^\oplus R^5R^6R^7X^\ominus$,

—$CO_2H$, —$CO_2^\ominus Y^\oplus$, —$CO_2R^4$, —$SO_2OR^5$, —$SO_2R^5$, —$SO_3^\ominus Y^\oplus$, —$PO(OR^5)OR^6$, —$PO(R^5)R^6$ and —C≡N, with the proviso that $R^2$ and $R^3$ cannot both be hydrogen; $R^4$ is alkyl and contains from 1 to 12 carbon atoms; $R^5$, $R^6$ and $R^7$ are individually selected from the group consisting of hydrogen and alkyl containing from 1 to 12 carbon atoms; $X^\ominus$ is an anion selected from the group consisting of chloride, bromide, iodide, bisulfate, acetate and methyl sulfate; $Y^\oplus$ is a cation selected from the group consisting of alkali metals, and ammonium and Z is selected from the group consisting of

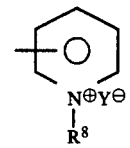

wherein $R^6$ is alkyl containing from 1 to 6 carbon atoms, and aromatic mono- and bicyclic heterocyclic groups wherein each ring contains 5 or 6 atoms including one or two heteroatoms selected from nitrogen, oxygen and sulfur with the proviso that Z cannot be pyridyl, furyl or thienyl when m is 0 and the heterocyclic groups are active-hydrogen free. The term "active hydrogen" refers to a hydrogen atom bonded to nitrogen or other group which makes the hydrogen atom reactive toward organometallic compounds such as organolithium and organosodium compounds.

DETAILED DESCRIPTION OF THE INVENTION

The present insecticidal tetraorganotin compounds contain four carbon-tin bonds, three of which are methyl groups. The fourth valence of the tin atom is satisfied by a substituted benzyl, substituted phenyl or monovalent aromatic heterocyclic group that is either monocyclic or bicyclic. The heterocyclic group can be either bonded directly to the tin atom through a cyclic carbon atom or separated from the tin atom by a methylene group. The heterocyclic group cannot be pyridyl, furyl or thienyl when it is bonded directly to the tin atom. The phenyl or benzyl group can contain monovalent substituents, represented by $R^1$, $R^2$ and $R^3$ in the preceding formulae. Alternatively, the substituent can be of the formula —O—$(CH_2)_p$O— wherein the two oxygen atoms are bonded to adjacent cyclic carbon atoms of a phenyl or benzyl group and p is the integer 1 or 2.

The nature and degree of activity exhibited by a given compound is greatly influenced by the fourth group attached to the tin atom. Phenyl- and hydrocarbyl- substituted phenyltrimethyltin compounds such as phenyltrimethyltin, o-tolytrimethyltin and p-xylyltrimethyltin are relatively inactive against insects, as will be demonstrated by the data in the accompanying examples. The compounds of this invention are structurally related to these inactive compounds but show unexpected insecticidal activity which in many cases is equal to or greater than that shown by certain commercial insecticides used as standards by those skilled in the art.

U.S. Pat. No. 3,988,145 discloses novel organotin compounds of the general formula A—SO$_2$CH$_2$SnR$_3^1$ where A is alkyl of from 1 to 14 carbon atoms, aryl, substituted aryl, or R$_2$N, where each R is alkyl of from 1 to 14 carbon atoms and each R$^1$ is alkyl of from 1 to 14 carbon atoms or aryl.

U.S. Pat. No. 3,987,191 discloses novel (organosulfinylmethyl) triorganotin compounds of the formula R—SO—CH$_2$SnR$_{31}$ where R is alkyl of from 1 to 14 carbon atoms, aryl or a substituted aryl group and each R$^1$ is an alkyl group of 1 to 10 carbon atoms. The compounds in the aforementioned patents allegedly exhibit insecticidal and acaricidal properties.

The compounds of the present invention differ from compounds disclosed in U.S. Pat. Nos. 3,988,145 and 3,987,191 in that a cyclic carbon atom of the aryl or heterocyclic group is bonded directly to the tin atom or is separated from the tin atom by only one methylene radical. No heteroatom is present in the linkage between the tin atom and the aryl or heterocyclic radical.

U.S. Pat. No. 3,976,672 claims (hydrocarbylphenylsulfonyl)alkyltrimethyl stannanes of the general formula

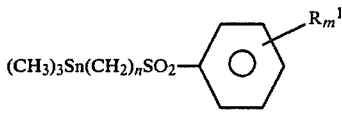

where each R$^1$ is the same or different and is linear or branched alkyl of from 1 to 20 carbon atoms, cycloaliphatic having 4 to 6 carbon atoms or linear or branched alkenyl having 2 to 20 carbon atoms, m is an integer from 1 to 3 and n is an integer from 2 to 11. The compounds of this invention differ from the compounds disclosed in U.S. Pat. No. 3,976,672 in two important aspects. A minimum of two methylene groups and a sulfur dioxide group are not required between the tin atom and the aryl group and the substitution on the aryl group is not an alkyl or other hydrocarbon radical. Data in the accompanying examples demonstrate that compounds wherein the substituent on the phenyl group is alkyl are relatively ineffective insecticides. Furthermore, the compounds disclosed in U.S. Pat. No. 3,976,672 are prepared using trimethyltin hydride, a volatile, unstable and highly toxic compound as one of the starting materials. This reagent is not employed to prepare the present compounds.

Certain of the present tetraorganotin compounds containing a substituted phenyl or a substituted benzyl group bonded to the tin atom are conveniently prepared by reacting the corresponding phenyl- or benzyl magnesium halide with trimethyltin chloride. The reaction of aryl magnesium compounds with stannic halides or organotin halides is well known and does not constitute any part of the present invention. Alternatively the compounds can be prepared by reacting trimethyltin lithium or trimethyltin sodium with a substituted halobenzene or α-halotoluene.

Those tetraorganotin compounds wherein Z in the foregoing formula represents a heterocyclic radical can be prepared by reacting the corresponding heterocyclic halide, such as 3-bromopyridine, with an alkyllithium compound and trimethyltin chloride. Alternatively, trimethyltin lithium or trimethyltin sodium is reacted with the heterocyclic halide. The accompanying examples contain detailed procedures for preparing both of the foregoing types of compounds.

The radical Z in the generic formula for the present tetraorganotin compounds represents an aromatic monocyclic or bicyclic residue wherein each ring contains 5 or 6 atoms, at least one of which is nitrogen, sulfur or oxygen atom. Suitable heterocyclic precursors for preparing this class of compounds can be represented by the formula Z—X wherein X is a halogen atom, preferably chlorine or bromine, that is bonded to a carbon atom. When the heterocyclic group represented by Z contains a nitrogen atom, the nitrogen cannot be bonded directly to a hydrogen atom, nor can Z contain any other labile hydrogen atoms. The reason for these requirements is that the labile hydrogen atom may react with the organometallic reagent used to prepare the final product, resulting in formation of a tinnitrogen bond or a stannic hydride. These classes of compounds are not within the scope of the present invention. When only two of the three valences of a nitrogen atom are satisfied by bonds to cyclic atoms of the "Z" group the remaining valence is preferably satisfied by a hydrocarbyl group such as alkyl.

Suitable aromatic heterocyclic precursors include halogen-containing N-hydrocarbyl pyrroles, N-hydrocarbyl pyrazoles, 2,2-dihydrocarbyl-1,3-isodiazoles and triazoles, isoxazole, oxazole, thiazole, isothiazole, oxadiazole, pyridazine, pyrimidine, pyrazine, the isomeric halogen-containing triazines, halogenated benzofuran, benzothiofuran, N-hydrocarbyl indoles, benzoxazole, quinoline and isoquinoline. While the exact nature of the hydrocarbon substituents specified for some of the foregoing heterocyclic compounds is not critical, lower alkyl containing from 1 to 4 carbon atoms is preferred.

The "Z" group may contain one or more substituents such as hydrocarbyl, alkoxy, N,N-dialkylamino, alkylthio and halogen atoms in addition to the halogen which reacts with the tin compound to form the present compounds.

Specific examples of preferred compounds include trimethyl-3,4-methylenedioxyphenyltin, trimethyl-5-pyrimidyltin, trimethyl-3-pyridyltin methiodide, trimethyl-p-carbethoxyphenyltin, trimethyl-p-chlorobenzyltin, trimethyl-p-methylbenzyltin, trimethyl-2-thienylmethyltin, trimethyl-2-naphthylmethyltin, trimethyl-p-biphenylmethyltin, trimethyl(p-N,N-diethylaminobenzyl)tin and the methiodide thereof and trimethyl4-potassiocarboxyphenyltin. The present tetraorganotin compounds effectively control insects on agricultural and ornamental crops.

For use as insecticides, the organotin compounds of this invention are preferably incorporated into compositions which comprise an inert carrier and one or more of the organotin compounds. (As used herein an inert carrier is defined as a solvent or a dry bulking agent which has substantially no insecticidal effectiveness but which provides a means whereby the organotin compounds can be diluted for convenient application). Such insecticidal compositions enable the organotin compounds to be applied in a convenient and controlled manner to plants in any desired quantity. These compositions can be solids, such as dusts, or granules or wettable powders, or they can be liquids such as solutions, aerosols, or emulstions. For application to plants the compositions generally contain from about 2 to 80% of the organotin compound depending on a number of factors such as physical properties and mammalian toxicity. The concentration of organotin compound in the final spray mixture will be generally in the range from about 1 to 1,000 ppm. (parts per million), preferably from about 10 to 500 ppm. Generally, whatever application technique is used, the amount of organotin compound applied should be of the order of from about 0.01 to about 3.0 pounds, preferably from about 0.1 to about 1.0 pound per acre of crop, depending on type of crop, foliage density and the severity of the infestation.

For convenience in bulk handling, the compositions are generally formulated as concentrates which can be diluted to the desired usage level with water, organic solvent or other inert carrier just prior to use.

Dusts can be prepared by blending the organotin compounds with a solid inert carrier such as talcs, clays, silicas, pyrophylite and the like. Granular formulations can be prepared by impregnating the organotin compounds, usually dissolved in a suitable solvent, onto and into granulated carriers such as the attapulgites or the vermiculites, usually of a particle size range of from about 0.3 to 1.5 mm., or by coating a solid inert carrier with a wettable powder formulation of the compounds. Wettable powders, which can be dispersed in water or oil to any desired concentration of the organotin compounds, can be prepared by incorporating wetting agents onto concentrated dust compositions.

The organotin compounds of the present invention are sufficiently soluble or dispersible in the common organic solvents such as kerosene, xylene, Stoddard Solvent, acetone, and the like, that they can be used directly as solutions or dispersions in these solvents. Frequently these solutions or dispersions are dispensed under super-atmospheric pressure as aerosols. Preferred liquid insecticidal compositions for the practice of the invention herein are emulsifiable concentrates which comprise the organotin compound, an emulsifier, and, as an inert carrier, a solvent. Such concentrates can be extended with water and/or oil to the desired concentration of organotin compound for application as sprays to the plants which are to be treated. The emulsifiers used in these concentrates are surface active agents of the anionic, nonionic, cationic, ampholytic or zwitterionic type and normally comprise from about 0.1% to 30% by weight of the concentrate. The emulsifiers can be used singly or in mixtures. Examples of suitable anionic surface active agents are alkali metal and alkaline earth metal (e.g., sodium and calcium) salts of fatty alcohol sufates having from 8–18 carbon atoms in the fatty chain and the alkali metal and alkaline earth metal (e.g., sodium and calcium) salts of alkyl benzene sulfonates, having from 9 to 15 carbon atoms in the alkyl chain. Examples of suitable nonionic surface active agents are the polyethylene oxide condensates of fatty alcohols, wherein the fatty chain contains from about 8 to 22 carbon atoms and the amount of ethylene oxide condensed onto each mole of fatty alcohol is from about 5 to 25 moles. Examples of suitable cationic surface active agents are dimethyl dialkyl quaternary ammonium salts wherein the alkyl chains contain from about 8 to 18 carbon atoms and the salt forming anion is a halogen. Examples of suitable ampholytic surface active agents are derivatives of aliphatic secondary or tertiary amines in which one of the aliphatic substituents contains from about 8 to 18 carbon atoms and one contains an anionic water solubilizing group, e.g., sulfate, sulfonate or carboxylate. Specific suitable ampholytic surface active agents are sodium-3-dodecylamino propionate and sodium-3-dodecylamino propane sulfonate. Examples of suitable Zwitterionic surface active agents are derivatives of aliphatic quaternary ammonium compounds in which one of the aliphatic constituents contains from about 8 to 18 carbon atoms and one contains an anionic water solubilizing group. Specific examples of Zwitterionic surface active agents are 3-(N,N-dimethyl-N-hexadecylammonio) propane-1-sulfonate and 3-(N,N-dimethyl-N-hexadecylammonio)-2-hydroxy propane-1-sulfonate. Many other suitable surface active agents are described in McCutchen's Detergents and Emulsifiers—1972 Ed., Allured Pub. Co., Ridgewood, N.J., which is incorporated by reference herein. Suitable solvents for these emulsifiable concentrates include hydrocarbons such as benzene, toluene, xylene, kerosene and Stoddard Solvent and halogenated hydrocarbons such as chlorobenzene, chloroform, fluorotrichloromethane and dichlorodifluoromethane. Solvents can be used singly or in mixtures.

The following examples describe the preparation of representative compounds encompassed by the accompanying claims and demonstrate the efficacy of these compounds as insecticides which can be applied to living plants. All parts and percentages are by weight unless otherwise specified.

EXAMPLE 1

Preparation of Trimethyl-3,4-methylenedioxyphenyltin

To a reaction vessel equipped with a mechanically driven agitator, water-cooled condenser, addition funnel, thermometer, and nitrogen inlet was added 0.15 mole of 3,4-methylenedioxyphenyl magnesium bromide in anhydrous tetrahydrofuran. The Grignard reagent was prepared by the addition of a solution of 41.5 g. (0.2 mole) of 3,4-methylene dioxybromobenzene in 200 cc. of anhydrous tetrahydrofuran to 7.29 g. (0.3 g. atoms) of magnesium turnings over 90 minutes at reflux temperature. The mixture was held at reflux temperature for an additional two hours, then cooled to room temperature and filtered to remove excess magnesium metal. A solution containing 30 g. (0.15 mole) of trimethyltin chloride in 150 cc. of anhydrous benzene was added to the Grignard reagent over 20 minutes while the reaction temperature was maintained at 20° C. by use of external cooling. The solution was stirred at room temperature for 17 hours and then hydrolyzed with 300 cc. of a saturated aqueous solution of ammonium chloride. The temperature of the reaction mixture was maintained below 40° C. during the hydrolysis. The aqueous phase was then separated from the organic phase and washed twice with 100 cc. of ether. The organic phases were combined, dried over a quantity of anhydrous magnesium sulfate, filtered and concentrated under reduced pressure. A black liquid was isolated (52.3 g.) which was distilled under reduced pressure (1.2 mm.) A clear, colorless liquid boiling at 106°–108° C. was collected (36.3 g.) and analyzed. The tin content was found to be 40.30%, and the chloride content was zero. The calculated tin content for trimethyl-3,4-methylenedioxyphenyltin is 41.67%. The refractive index was recorded as 1.555 $D^{23}$. Gas chromatographic analysis indicated a purity of 96%. The infrared spectrum of the neat liquid contained absorption bands at 1220 and 1029 cm$^{-1}$ indicative of a C—O—C stretch for alkyl aryl ethers. The nuclear magnetic resonance spectrum contained a singlet at 0.25 ppm. (CH$_3$—Sn, 9H's), a singlet at 5.83 ppm. (—O—CH₂—O—, 2H's), and a multiplet centered at 6.95 ppm. (phenyl—C—H, 3H's).

EXAMPLE 2

Preparation of Trimethyl-4-carbethoxyphenyltin

To a reaction vessel equipped with a mechanically driven agitator, water-cooled condenser, addition funnel, thermometer, and nitrogen inlet was added 80 cc. of anhydrous diethyl ether of diethylene glycol and 8 g. (0.35 mole) of freshly cut sodium pieces. The mixture was cooled to −2° C. and a solution of 52.4 g. (0.16 mole) of hexamethylditin in 80 cc. of anhydrous diethyl ether of diethylene glycol was added over 20 minutes. The hazy green mixture was stirred for one additional hour at 0° C. and then allowed to warm to room temperature over three hours. The mixture was filtered and then added dropwise over a 2.5 hour period to a solution of 36.6 g. (0.16 mole) ethyl-p-bromobenzoate in 160 cc. of the diethyl ether of diethylene glycol, cooled to −15° C. The solution was stirred 2 hours at −2° C. and 16 hours at room temperature. The solution was then hydrolyzed using 300 cc. of a 5% aqueous citric acid solution. The water phase was separated from the organic phase and washed twice with 200 cc. portions of ether. The organic layers were combined, dried over a quantity of magnesium sulfate, and concentrated under reduced pressure. The solvent was removed at 50 mm. pressure (mercury manometer) and the residue distilled at 0.15 mm. A clear liquid fraction boiling at 88°–90° C. was isolated and analyzed. The tin content was found to be 37.54%. The calculated tin content for carbethoxyphenyltin is 37.92%. Gas chromatographic analysis indicated a purity of 97.6%. The refractive index was recorded as 1.5362 at 23° C. The nuclear magnetic resonance spectrum contained a singlet at 0.38 ppm. (CH₃—Sn, 9H's), a triplet at 1.46 ppm. (CH₃—,3H's), a quartet at 4.50 ppm.

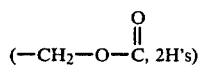

and a doublet of doublets at 7.86 ppm.

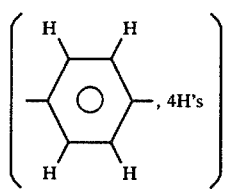

EXAMPLE 3

Preparation of Trimethyl-4-potassiocarboxyphenyltin

To a reaction vessel equipped with a mechanically driven agitator, water-cooled condenser, thermometer and nitrogen inlet was added a solution containing 3.23 g. (0.010 mole) of trimethyl-4-carbethoxyphenyltin and 25 cc. of methanol. A solution containing 0.73 g. (0.013 mole) of potassium hydroxide dissolved in 25 cc. of 90% methanol and 10% water was added at once and the resulting solution was stirred for 23 hours at room temperature, and 25 hours at the boiling point. An additional 0.11 g. of potassium hydroxide was added and heating at the boiling point was continued for 2.5 hours, followed by 16 hours of stirring at room temperature. The solvent was removed under reduced pressure and the resultant white solids were dried and analyzed. The tin content was found to be 31.53% and the potassium content was 14.71%. The calculated tin and potassium values for trimethyl-4-potassiocarboxyphenyltin are 36.75% and 12.11%, respectively.

EXAMPLE 4

Preparation of Trimethyl-3-pyridyltin

To a reaction vessel equipped with a mechanically driven agitator, water-cooled condenser, addition funnel, thermometer, and nitrogen inlet was added a solution containing 17.1 g. (0.108 mole) of 3-bromopyridine in 150 cc. of anhydrous ether. The solution was cooled to −50° C. using a dry ice-acetone bath. By a dropwise addition, 40 cc. (0.108 mole) of n-butyllithium in n-hexane was added over 14 minutes. The resulting yellow-orange solution was stirred for an additional 60 minutes. A solution containing 17.9 g. (0.09 mole) of trimethyltin chloride in 150 cc. of anhydrous benzene was added over 40 minutes, followed by a 75 minute stirring period. The dark orange solution was warmed to room temperature and stirred 18 hours before being hydrolyzed with a saturated aqueous solution of ammonium chloride. The aqueous phase was separated from the organic phase and washed with 200 cc. of ether. The organic portions were combined, dried over a quantity of anhydrous magnesium sulfate, filtered and concentrated under reduced pressure. A dark red liquid (16.2 g.) was isolated and distilled under reduced pressure (0.1–0.2 mm.). A clear, colorless liquid fraction boiling at 50°–60° C. was collected and redistilled (6.5 mm.). The fraction boiling at 100°–103° C. was collected and analyzed. The tin content was found to be 48.89%. The calculated tin content for trimethyl-3-pyridyltin is 49.07%. Gas chromatographic analysis indicated a purity of 98% and the refractive index was recorded as 1.5399 at 25° C. The nuclear magnetic resonance spectrum contained a singlet at 0.33 ppm. (CH₃—Sn, 9H's), a complex multiplet centered at 7.2 ppm. (β-pyridyl H, 1H), a doublet of triplets at 7.75 ppm. (γ-pyridyl H, 1H), a doublet of doublets at 8.52 ppm. (γ-pyridyl H on 6 carbon, 1H), and a doublet at 8.65 ppm. (γ-pyridyl H on 2 carbon, 1H) in agreement with the expected structure.

EXAMPLE 5

Preparation of Trimethyl-3-pyridyltin Methiodide

A 250 cc. capacity round-bottom flask was charged with 3.5 g. (0.014 mole) of trimethyl-3-pyridyltin and 15 cc. (0.24 mole) of methyl iodide. The flask was fitted with a reflux condenser and a tube containing anhydrous calcium sulfate and the contents were stirred while being heated at reflux temperature for three hours. The solution was allowed to cool to ambient temperature and stirred for 17 hours. At the end of this period the solution was concentrated to dryness under reduced pressure. The resultant yellow solids were washed with 50 cc. of hexane and dried under reduced pressure for 18 hours. The dried solids (3.3 g.) melted from 137°–143° C. Upon analysis the solid was found to contain 30.91% tin and 32.5% iodine. The calculated analysis for the expected product, trimethyl-3-pyridyltin methiodide, is 30.90% tin and 33.0% iodine. The nuclear magnetic resonance spectrum, obtained using a solution of the compound in deuterated chloroform, contained a singlet at 0.47 ppm. (CH₃—Sn, 9H's), a singlet at 4.61 ppm. (CH₃—N⊕, 3H's), a multiplet centered at 7.9 ppm.

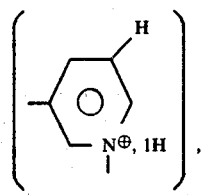

a complex doublet at 8.49 ppm.

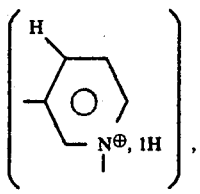

and a multiplet centered at 9.2 ppm.

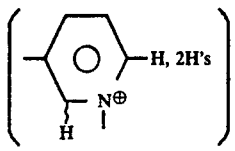

all of which are consistent with the expected structure.

EXAMPLE 6

Preparation of Trimethyl-5-pyrimidyltin

To a reaction vessel equipped with a mechanically driven agitator, water cooled condenser, addition funnel, thermometer, and nitrogen inlet was added a solution containing 47.7 g. (0.3 mole) of 5-bromopyrimidine in 300 cc. of anhydrous ether and 300 cc. of anhydrous tetrahydrofuran. The solution was cooled to −110° C. using an ethyl alcohol-liquid nitrogen bath. By a dropwise addition, 120 cc. (0.3 mole) of n-butyllithium in n-hexane was added over 50 minutes. The solution was stirred for an additional 3.5 hours. A solution containing 49.8 g. (0.25 mole) of trimethyltin chloride in 150 cc. of anhydrous tetrahydrofuran was added over 60 minutes. After 10 minutes of stirring at −110° C. the orange mixture solidified and stirring was discontinued. The mixture was allowed to warm to −32° C. over 16 hours during which time it liquified and stirring was resumed for 4 hours. The mixture was hydrolyzed with 300 cc. of a saturated aqueous solution of ammonium chloride plus an additional 100 cc. of water. The aqueous phase was separated from the organic phase and washed with 250 cc. of ether. The organic portions were combined, washed twice with 500 cc. of water, separated, dried over anhydrous magnesium sulfate, filtered, and concentrated under reduced pressure. The dark orange residue was distilled under reduced pressure (19 mm.). A clear colorless liquid fraction (35.2 g.) boiling at 118°–122° C. was collected and found to be 90% pure by gas chromatography. The liquid was redistilled under reduced pressure (19 mm.) and the clear fraction boiling between 119°–120° C. was collected and analyzed. The tin content was found to be 48.14% while the nitrogen content was 11.82%. The calculated tin and nitrogen contents for trimethyl-5-pyrimidyltin are 48.87% and 11.53%, respectively. Gas chromatographic analysis indicated a purity of 97% and the refractive index was recorded as 1.5349 at 25° C. The nuclear magnetic resonance spectrum contained a singlet at 0.38 pp. (CH₃—Sn, 9H's), a triplet at 8.7 ppm. (α-pyrimidyl H's, 2H's), and a singlet at 9.12 ppm. (γ-pyrimidyl H, 1H), all consistent with the expected structure.

A number of representative compounds were evaluated to determine their efficacy as control agents for the beet armyworm (*Spodoptera exigua*), tobacco budworm (*Heliothis virescens*), larvae of the codling moth (*Laspeyresia pomonella*), western spotted cucumber beetle (*Diabrotica undecimpunctata*) and peach aphid (*Myzus persicae*).

The compounds evaluated were applied to plants in the form of aqueous dispersions containing the desired concentration of organotin compound. Solid compounds were combined with a small amount of a wettable powder to form a concentrate, which was subsequently diluted to the final concentration with water containing 0.5% of a commercial anionic surfactant. Liquid compounds were dissolved in a small amount of acetone and the resultant concentrate was brought to the final dilution using water containing 0.5% of the aforementioned anionic surfactant.

The following procedures were employed to evaluate the efficacy of representative compounds as control agents for the aforementioned insects.

PROCEDURE 1

Beet Armyworm

A cotton plant was grown until it developed two fully expanded leaves. The plant was then dipped into an aqueous dispersion of the test compound and allowed to dry for 30 minutes. The two fully expanded leaves were then removed and placed in petri dishes. Five third instar larvae of the beet armyworm were placed in each dish. The dishes were stored for six days in a chamber maintained at a temperature of 26°–27° C. and a relative humidity of 80%, at the end of which time a mortality count was taken.

PROCEDURE 2

Tobacco Budworm (Stomach and Contact Test)

Newly developed tobacco leaves were treated as described for the cotton plants in Procedure 1. A section of the leaf was then placed in a petri dish. Larvae of the tobacco budworm were placed on the treated leaves, which were then stored for two days at 26°–27° C. and 80% relative humidity, at the end of which time a mortality count was taken.

PROCEDURE 3

Codling Moth Larvae

An aqueous dispersion of the test chemical was applied to apples or pears, which were then covered with eggs of the codling moth. The eggs had previously been dipped in the same aqueous dispersion applied to the fruit. The fruit was then incubated from eight to ten days in a greenhouse, at which time the percentage of living larvae was determined and compared with the results from a sample of untreated fruit used as a control.

PROCEDURE 4

Western Spotted Cucumber Beetle Larvae

Seventy-five grams of air-dried soil were placed in a 236 cc. capacity round bottle and treated with sufficient volume of a solution containing 400 ppm. of the chemical to give 25 ppm. of toxicant on an air-dried soil basis. The treated soil, after being allowed to air dry, was mixed by shaking and rolling.

Eggs of the western spotted cucumber beetle (laid over a period of 3 or 4 days) were collected and a measured quantity of eggs were suspended in water. The egg concentration was 70–80 eggs/0.5 cc. of solution. A portion of the suspension containing about 50 eggs was pipetted into the bottom of a clear plastic medicinal vial. An amount of treated soil sufficient to cover the eggs was added, a corn seed was placed on the soil and covered with additional treated soil.

The soil, eggs and seed mix was watered and additional water added as necessary to maintain growth of the seedling corn plant. Care was taken not to add excess water sufficient to drown the larvae. After a period of from 6–9 days an observation was made to determine the presence of larvae both on top of the soil and at the roots of the seedling.

PROCEDURE 5

Peach Aphid

Cotton plants were grown singly in small square pots. Before the leaves were fully expanded the plant was infested by placing the leaves in contact with leaves from plants which had previously been infested with peach aphids. An aqueous dispersion of the test chemical was then injected into the root zone of the infested plants, and the plants were kept in a greenhouse for from three to six days following treatment with the test compound, at which time a mortality count was made A number of the preferred tetraorganotin compounds were evaluated as insecticides using the foregoing procedures. The results of these evaluations are summarized in the following table. The efficacy of the compounds listed is expressed using the term $LC_x$, which represents the concentration in parts per million (ppm.) that was lethal to a specified percentage of the population, indicated by "x". All initial screening of the compounds was done at a concentration of 400 ppm. except for the western spotted cucumber beetle, in which instance the concentration was 25 ppm.

| Compound $(CH_3)_3SnR$ R= | BAW $(LC_{100})$ | TBW $(LC_{100})$ | CML $(LC_{70})$ | WSCB $(LC_{100})$ | PA $(LC_{95})$ |
|---|---|---|---|---|---|
| 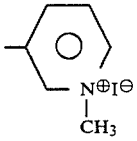 | <25 | <25 | <25 | <1.5 | — |
| 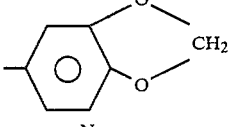 | — | <25 | 25 | — | — |
| 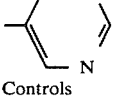 | — | <25 | — | — | 100 |
| Controls | | | | | |
| phenyl | >400 | >400 | >400 | >25 | >400 |
| o-tolyl | >400 | >400 | — | — | >400 |
| 2,5 xylyl | >400 | >400 | >400 | >25 | >400 |

BAW = Beet Armyworm
TBW = Tobacco Budworm
CML = Codling Moth Larvae
WSCB = Western Spotted Cucumber Beetle
PA = Peach Aphid

What is claimed is:

1. A novel tetraorganotin compound of the formula

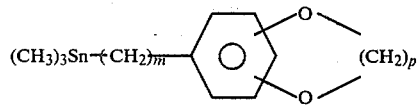

wherein said —O—(CH$_2$)$_p$O— group is bonded to adjacent carbon atoms of the phenyl ring, m is 0 or 1 and p is 1 or 2.

2. A compound according to claim 1 of the formula

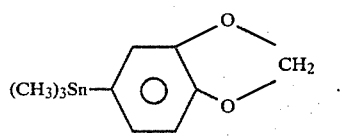

* * * * *